United States Patent
Kerschbaumer et al.

(10) Patent No.: US 6,743,014 B2
(45) Date of Patent: Jun. 1, 2004

(54) SHADE DETERMINATION APPARATUS AND METHOD FOR SPECIFYING AND DETERMINING COLORS FOR TEETH AND DENTAL RESTORATIONS

(75) Inventors: Harald Kerschbaumer, Klaus (AT); Armin Ospelt, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 264 days.

(21) Appl. No.: 10/004,181

(22) Filed: Oct. 31, 2001

(65) Prior Publication Data

US 2002/0081547 A1 Jun. 27, 2002

Related U.S. Application Data

(63) Continuation-in-part of application No. 09/821,567, filed on Mar. 29, 2001, now Pat. No. 6,499,998.
(60) Provisional application No. 60/215,829, filed on Jul. 3, 2000.

(30) Foreign Application Priority Data

May 16, 2000 (DE) .......................................... 100 23 840

(51) Int. Cl.[7] .............................................. A61C 19/10
(52) U.S. Cl. ..................................... 433/26; 433/203.1
(58) Field of Search ................................. 433/26, 203.1, 433/215, 29

(56) References Cited

U.S. PATENT DOCUMENTS

| | | | |
|---|---|---|---|
| 3,405,446 A | 10/1968 | Wiener | 32/1 |
| 4,654,794 A | 3/1987 | O'Brien | |
| 4,836,674 A | 6/1989 | Lequime et al. | 356/319 |
| 5,177,694 A | 1/1993 | Graham et al. | 364/526 |
| 5,240,414 A | 8/1993 | Thompson | 433/26 |
| 5,273,429 A | 12/1993 | Rekow et al. | 433/215 |
| 5,690,486 A | 11/1997 | Zigelbaum | 433/29 |
| 5,766,006 A | 6/1998 | Murljacic | 433/26 |
| 5,800,164 A | 9/1998 | Pfau | 433/26 |
| 5,961,324 A | * 10/1999 | Lehmann | 433/26 |
| 6,058,357 A | 5/2000 | Granger | |
| 6,132,210 A | 10/2000 | Lehmann | 433/26 |
| 6,190,170 B1 | 2/2001 | Morris et al. | 433/215 |
| 6,206,691 B1 | 3/2001 | Lehmann et al. | 433/26 |
| 6,210,159 B1 | 4/2001 | Lehmann et al. | 433/26 |
| 6,331,113 B1 | 12/2001 | Morris et al. | |
| 6,561,800 B2 | 5/2003 | Lehmann | |
| 6,575,751 B1 | 6/2003 | Lehmann et al. | |

FOREIGN PATENT DOCUMENTS

| | | |
|---|---|---|
| DE | 26 41 740 | 5/1978 |
| DE | 19611122 | 9/1997 |

* cited by examiner

*Primary Examiner*—Cary E. O'Connor
(74) *Attorney, Agent, or Firm*—Winston & Strawn LLP

(57) ABSTRACT

In a shade determination apparatus for teeth and dental restorations, a set of reference templates for comparing to a patient's tooth is provided. Based on the coloration of the reference template, the shade of a tooth or of a restoration to be employed can be determined. The reference templates are produced in a layer arrangement, taking into consideration layer thickness, material selection, or both, that corresponds to the tooth or the dental restoration to be employed. A storage apparatus stores the coloration of the reference templates, and the layering of the tooth or of the dental restoration can be matched and determined based on partial images from an image of the patient's tooth.

18 Claims, 2 Drawing Sheets

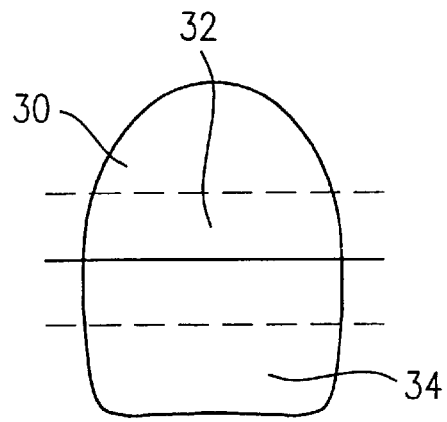
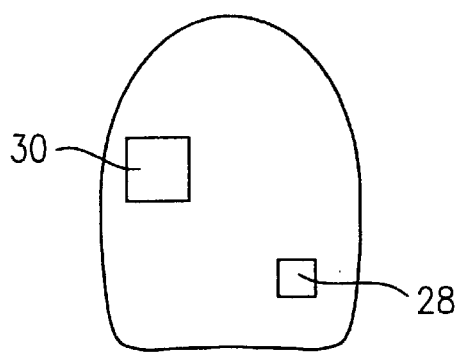
Fig. 7            Fig. 8
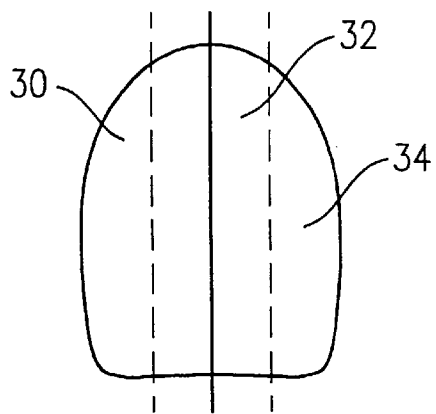
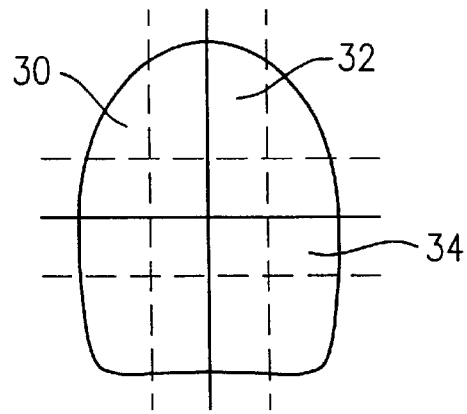
Fig. 9            Fig. 10

SHADE DETERMINATION APPARATUS AND METHOD FOR SPECIFYING AND DETERMINING COLORS FOR TEETH AND DENTAL RESTORATIONS

CROSS-REFERENCE TO RELATED APPLICATIONS

This application is a continuation-in-part of application Ser. No. 09/821,567, filed Mar. 29, 2001, now U.S. Pat. No. 6,499,998, which claims priority to provisional application No. 60/215,829, filed Jul. 3, 2000, each of which is incorporated herein by express reference thereto.

BACKGROUND OF THE INVENTION

The present invention relates to a shade or color determination apparatus for teeth and dental restorations, and also relates to a method for specifying and determining shades for teeth and dental restorations.

Such a shade determination apparatus and such a method are known from U.S. Pat. No. 5,766,006 ("the '006 patent"). This solution represents an advance relative to the use of a conventional shade guide. A commercial shade guide has a plurality of color groups, whereby in each group are located teeth with different color saturation and brightness and each group is assigned to a certain shade. The tooth in a shade guide can have a structure of one to five layers.

Such a shade guide has limited selection options. This limitation is not due to a lack of options for producing different color mixtures, but rather to the fact that even experienced dentists are limited in their ability to determine a shade correctly. One reason for this is that the eye becomes fatigued after long periods of comparison. But it is also due to the fact that the eye must observe the natural tooth and the prosthetic tooth held next to it in the shade guide in an "integrated" manner in order to obtain the results of the comparison. As a rule, the tooth in the shade guide has a two-layer structure and an overall thickness of 5 mm, whereby in the incisal region enamel material is applied thicker and in the cervical region dentine material is applied thicker.

An additional problem in the assessability of the reference teeth in the shade guide is that the teeth in the shade guide regularly comprise ceramics fired at high temperatures. Although such ceramics are more cost effective in terms of manufacture, manufacturing costs are substantial since they have to be distributed to all of the dentists. Today, however, it is not unusual for other ceramics to be used that are fired at temperatures lower than, e.g., 1300° C. The newest materials for dental restorations always have optical properties that are similar to teeth, e.g., opal effects or brightness values determined by precisely-defined crystal sizes, whereby the optical refraction index is adjusted. Shade guides used in the past are generally not well suited for comparing shades with these new materials. The materials d.SIGN® and Empress 2™ are also among the new materials that have enhanced brightness even with better translucence. The shade guides that were used in the past are generally not well suited for comparing shades with these new materials.

In this regard, systems like that of the '006 patent are not helpful because they use the known shade guides as the reference. Since these are not accurate despite the tooth-like structure of their coloration, especially for particularly translucent teeth, however, such computer-supported systems only result in minor improvements despite the expense they involve.

Another problem that in the past could only be addressed unsatisfactorily, if at all, is the progression of both the color and the translucence from the cervical to the incisal region. The cervical region generally has a coloration that tends toward reddish and is a bit transparent. The prior art provides no or only minimal accommodations for this graduation.

SUMMARY OF THE INVENTION

The invention relates to a shade determination apparatus and a corresponding method that are able to provide a tooth or a dental restoration in an aesthetically pleasing manner, whereby the shade comparison is made substantially easier for the dentist and laboratory, in particular by easily matching and reproducibly matching the coloration and translucence with adjacent teeth.

The present method is used for determining a patient's tooth shade for replacement or restoration thereof. This method includes the steps of: generating at least a partial electronic image of a patient's tooth wherein the image includes color information representative of the patient's tooth shade; electronically storing color information representative of a plurality of tooth shades in the form of a set of reference templates produced in a layer arrangement and including at least one of layer thickness or material selection; and comparing the color information of the image with the stored tooth shade color information to identify reference templates that may be used to prepare a tooth replacement or restoration having a color that corresponds to the patient's tooth shade.

The image of the patient's tooth can be visually or electronically compared to the stored color information. Advantageously, each reference template includes one or more layers of dentine material, incisal material, or opaque material. For optimum results, the comparing of color information and the identification of the reference template(s) is performed by a computer. If desired, the computer can control a CIM apparatus by which the layering of the replacement tooth or restoration to be manufactured can be determined in terms of material selection and layer thickness so that the replacement tooth or restoration can at least be pre-fabricated. The reference templates are preferably made of materials that are fired at the same temperature and same firing curve as the materials that are to be used for the replacement tooth or restoration to provide the closest color match.

A full image of the patient's tooth may be mapped with color pixels to assist in determining the color of the patient's tooth shade. Thus, a matching reference template is determined by selecting one or more pixels of the image, which pixels correspond to differential spatial locations of the patient's tooth, that provide similar color information and electronically comparing that color information with the stored reference template color information to determine the color of that portion of the patient's tooth. The patient's tooth pixel colors can be projected onto a display with the reference templates viewable on the display adjacent the patient's tooth so that optimum visual color matches can be made. Alternatively, the patient's tooth color can be determined by averaging the color information at selected pixel locations of the image before electronically comparing the averaged color information with the stored reference template color information.

The selection of the pixel(s) and determination of reference template(s) are generally repeated until a tooth shade color is determined for vertical or horizontal partitions, or both, of the tooth and until all the tooth shade color is determined for all spatial locations of the image of the patient's tooth. Prior to producing the replacement tooth or tooth restoration, the selected reference template(s) can be overlaid on the tooth shape on a display or monitor so that a virtual tooth replacement or restoration can be viewed along with an adjacent tooth or teeth. A digital camera can be utilized to obtain the image of the patient's tooth and the same camera or similar metamerical conditions can be used to obtain the color information of the reference templates before electronically storing the color information of the reference templates.

The patient's tooth shade color(s) and selected reference template(s) can be electronically stored on an electronic storage medium which is subsequently forwarded to a dental laboratory for use in construction of a replacement tooth or reconstruction of the patient's tooth. The electronic storage medium may be transmitted to the dental laboratory over a communications network. The electronic medium includes computer memory, a diskette, or a compact disk and the communications network comprises a computer, e-mail or the internet. If desired, preferred tooth shapes, incisal edges or tooth preparations can be electronically stored to assist the dentist in enhancing the preparation of the patient's tooth or the shape or incisal edge of the restoration or replacement tooth to provide improved smile appearance or improved biting or chewing performance.

In preparing the dental restoration or replacement tooth, one or a plurality of layers of dentine material, enamel material or opaque material can be applied on a dental alloy to a desired thickness to produce a tooth or restoration having the desired color. Preferably, each layer has a thickness of between about 0.3 and 3 mm and the materials are made of glass-ceramics or fiber-reinforced plastic.

BRIEF DESCRIPTION OF THE DRAWINGS

Additional advantages, details, and features can be ascertained from the following description of exemplary embodiments with the aid of the accompanying schematic drawings, in which:

FIG. 7 illustrates two alternatives for horizontal partitioning;

FIG. 8 illustrates variable fields for field partitioning;

FIG. 9 illustrates vertical fields for field partitioning;

FIG. 10 illustrates field partitioning with combined vertical and horizontal partitioning.

DETAILED DESCRIPTION OF THE INVENTION

Figure 1:
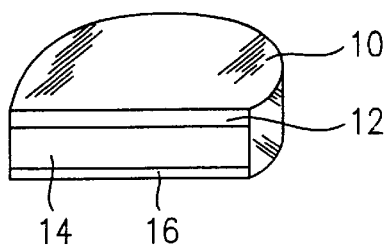
FIG. 1 is a perspective side elevation of a first reference template.

As used herein, the term "dentist," also includes a dental assistant, such as a hygienist.

The apparatus and method of the present invention provide a set of reference templates for comparison to a patient's tooth, whereby the shade of a tooth or a restoration that is to be employed can be determined based on the coloration of the reference template. These reference templates facilitate reproduction or restoration of the tooth by the laboratory by providing a layer arrangement, taking into consideration layer thickness and/or material selection that corresponds to the tooth, dental restoration, or filling that is to be employed. The apparatus also has storage means in which the coloration of the reference template is stored so that the layering of the tooth or dental restoration can be matched and determined based on partial images from an image of the patient's tooth.

Surprisingly, the present inventive measures make it possible to obtain adequate coloration, even in terms of perception of the human eye, for the tooth to be replaced or for dental restorations. This is believed to be based on the fact that the reference templates are provided with layer thicknesses that correspond to the actual layer thicknesses of the incisal material and dentin material to be applied. Surprisingly, this measure makes it possible to obtain a more natural appearance, even when the reference template is not in the shape of a tooth, because by recording the image with the same camera, the same assessment flows into the process for analyzing the natural tooth and the reference template. In this context it is important to reference the shades even if the same camera is not used, as an identical model camera may be used. In order to prevent metamerism effects, it is advantageous to provide identical lighting when generating the images.

In accordance with the invention, it is advantageous to select the layer thicknesses to correspond to the layer thicknesses that occur in practice. For instance, a set of reference templates can be produced with layer thicknesses: incisal material about 0.2 mm, dentine about 1 mm, and opaque layer about 0.1 mm. An additional set of reference templates can be produced with the layer thicknesses: incisal material about 0.2 mm, dentine material about 0.3 mm, and opaque layer about 0.1 mm. An additional set can be produced with the layer thicknesses: incisal material about 0.15 mm, dentine about 0.4 mm, deep dentine about 0.3 mm, and opaque layer about 0.1 mm.

In accordance with the invention, it is particularly advantageous in this context that the different colorations can be matched by means of an automatic comparison. It is preferable in this context for the recorded natural tooth to be displayed on a video screen or display with sections of this tooth marked in a suitable manner, and then to find the correct reference template immediately, so that the matching reference template can be selected as appropriate. In accordance with the invention, it is particularly advantageous for the reference templates to have been fired from original materials in the original layer thickness, cost-related issues not having a negative impact thereupon. On the contrary, it is no longer necessary to divide up shade guides oneself; rather, reference templates can simply be produced with laboratory quality, the appropriate detectable parameters for the reference template then being recorded with a reference camera and stored in a database. Even if procurement of the recording apparatus and the necessary software represents a certain monetary outlay, modified shades obtained in new materials or other types of shades can then be made available to the dentist or dental technician with no other measures required.

The accuracy of the comparison can be performed in accordance with the invention depending on the number of reference templates available in the database such that color differences are no longer visually perceptible. In accordance with the invention, it is advantageous when the regions of the tooth to be analyzed are pre-specified as the regions that are generally particularly critical. When the dentist wants to deviate from the standards, this can be done with no further action required by selecting other surfaces, whereby it is understood that the dentist also pre-specifies the type of material he or she wants, e.g., plastic or ceramic, and also pre-specifies whether or not an opaque layer will be used for facing metal frameworks.

In accordance with the invention, it is particularly advantageous that the shade determination apparatus determines the layers in terms of material selection, layer thickness, and combination of materials for every section of the tooth or tooth restoration that is to be blended in with the analyzed natural tooth. Thus the dental laboratory obtains precise information about how the restoration should be performed. It is also possible to pre-select the complexity of each different stage of the restoration. For instance, a switch can be provided for "complex" and "simple" instructions, which switch then pre-specifies more complex or simpler layers, as desired. As certain teeth as well as certain layers are more visible than others, the more complex instructions are preferred for these.

An additional parameter that must be determined for the dentist's or dental technician's comparison to the reference template is the layer thickness that will be available for a restoration. In this case as well, there is an automatic comparison with the best option, since the reference templates are available in different overall layer thicknesses so that the different shades can be taken into account and included automatically in the assessment.

FIG. 1 illustrates a reference template as an example of a plurality of similar reference templates with the same layer thickness, with different colorations in the individual layers. The reference template 10 is formed as a circular tablet in the exemplary embodiment illustrated, but any other desired shapes can also be used. The reference template 10 has an overall thickness of about 0.4 mm to 1.2 mm. The reference template comprises three or more layers, i.e., at least an enamel material layer 12 of about 0.1 mm to 0.3 mm, a dentine material layer 14 of about 0.25 mm to 0.75 mm, and an opaque layer 16 of about 0.05 mm to 0.5 mm. An exemplary reference template can be 3 layers and have thicknesses of 0.2 mm, 0.5 mm, and 0.1 mm, respectively.

Such reference templates are now manufactured in a plurality of combinations in this layer thickness and recorded by means of a digital camera. In one embodiment, the diameter of a reference template disk 10 is about 10 mm, i.e., it is generally larger than a tooth in a labial or buccal view. For instance, 24 reference templates can be produced in this layer structure that have different colorations for the three provided layers, i.e., enamel material 12, dental material 14, and opaque layer 16. The reference templates are produced from originals, e.g., from d.SIGN® dental ceramics shade standards, so that they correspond to the actual layers in the tooth.

Figure 2:
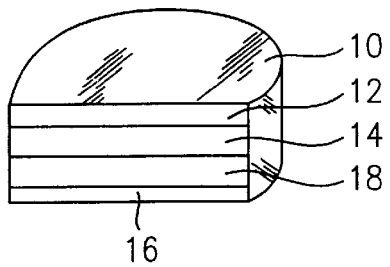
FIG. 2 is a perspective view of a second reference template.
Figure 3:
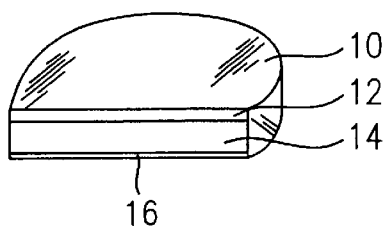
FIG. 3 is a perspective view of a third reference template.

FIG. 2 illustrates a modified structure of a reference template. The overall layer thickness of the reference template 10 in accordance with FIG. 2 is about 1.3 mm. To facilitate illustration, the layer thicknesses in FIGS. 1–3 are exaggerated relative to the diameter of the reference template. The enamel material 12 has a thickness of about 0.3 mm. Adjacent thereto is a dentine material layer 14 in which the layer thickness is about 0.4 mm. Adjacent thereto is a layer made of a deep dentine material 18 that also has a thickness of about 0.4 mm. The bottom-most layer is again an opaque layer 16 with a thickness of about 0.2 mm.

To facilitate handling, the reference templates can be applied to any desired base ceramic. Since the opaque layer already completely faces at a thickness of about 0.1 mm, the base layer for assessing the reference template is unimportant in terms of optics.

While the illustrated reference templates concern facing or veneered ceramics that are provided for restorations on a metal framework, reference templates made of ceramics for non-metal restorations can also be produced. For instance, the Empress 2™ ceramic product series can be used. Plastics, such as TARGIS® and VECTRIS® restoration materials, may also be used.

While the reference template 10 in FIG. 1 is constructed with three layers, the reference template 10 in FIG. 2 has four layers. The reference template 10 in FIG. 2 can consequently be considered more complex and the reference template 10 in FIG. 1 can be considered more simple. Of course, instead of using the deep-dentine material 18 for the reference template in FIG. 2, it is also possible to use clear material, which results in a more translucent effect.

Another reference template 10 is shown in FIG. 3 that has a minimum overall layer thickness of only about 0.66 mm. Provided in this case is a combination of about 0.12 mm enamel material 12, about 0.4 mm dentine material 14, and about 0.08 mm opaque layer 16.

As suitable materials are developed in the future that are appropriate for even thinner layer thicknesses, these can also be prepared and analyzed as reference templates in accordance with the invention.

Figure 4:
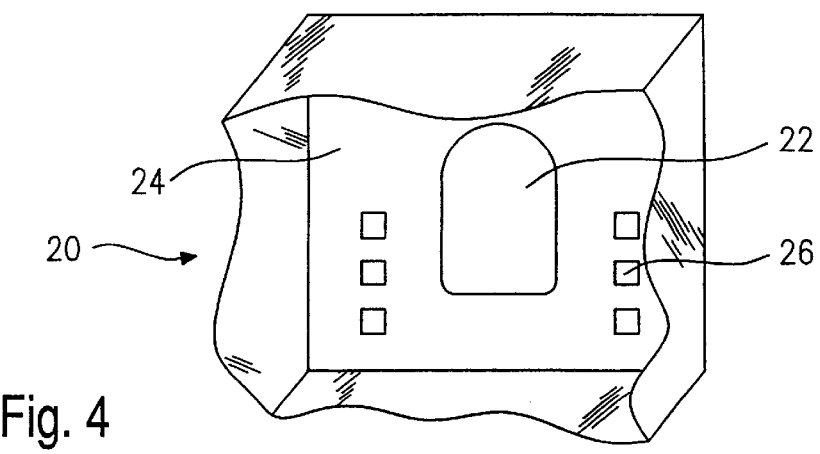
FIG. 4 is a perspective view of a receiving sheath.

The reference templates are preferably analyzed in the same manner that the patient's teeth are later analyzed. Provided for this is a covering sheath 20, illustrated in FIG. 4, that is black in color on the inside and that has a recess 22 that substantially corresponds to the labial or buccal view of a tooth. The recess 22 is embodied in an end 24 of the sheath that is black on the inside, while the digital camera (not shown) is attached to the opposing end.

Such a covering sheath 20 not only fulfills the function of blocking out ambient light, it also ensures the correct distance between tooth and optics. In addition, it can be used to house one or more shade reference templates that can be arranged, in one embodiment, adjacent to the side of the incisal edge of the tooth.

In an alternative embodiment, instead of a cover in the shape of a tooth, some other type of cover is provided. In a further embodiment, the shade reference template is positioned by means of an appropriate holder immediately below, rather than adjacent the side, of the incisal edge of the tooth.

Lateral to the recess 22, but clearly spaced therefrom, are provided a plurality of reference shade fields 26 that can be used for individual shade comparisons. It is important that these reference shades be extremely color-stable so that consideration should also be given to manufacturing them from ceramic materials to achieve this.

For recording the reference template, the reference template is now placed on the other side of the recess 22. The reference template is larger than the recess 22, so that it covers the recess 22 completely. A source of light is provided in the illustrated exemplary embodiment on the nearer side of the recess 22. The light source can either be integrated into the cover sheath 20 or connected from outside, whereby the light then strikes the end 24 preferably via a mirror. The light intensity is regulated by, for example, the digital camera so that identical lighting is always maintained.

The reference templates are now recorded successively, and the values obtained for the various possible recorded parameters are stored in a database and assigned to the reference template. For example, a total of about 1000 templates is appropriate for the different materials in numerous different combinations of layer thicknesses and colorations.

Figure 5:
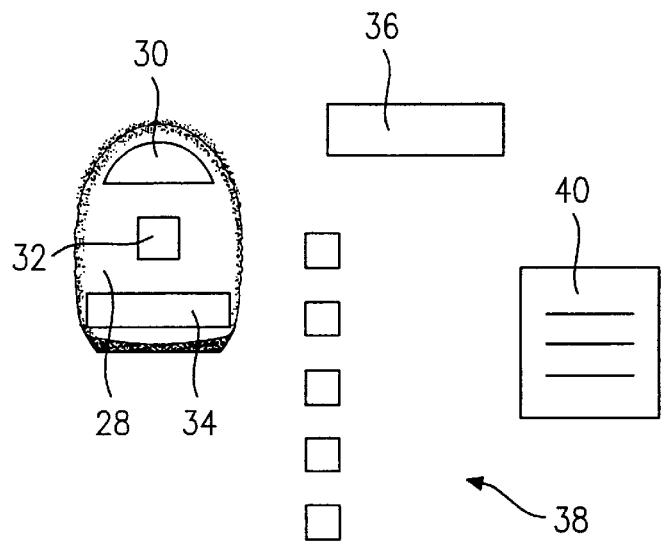
FIG. 5 illustrates a view of a screen of a color analyzing apparatus in accordance with the invention.

The data are made available to the dental laboratory or dental practice, together with an appropriate program, the digital camera, and the covering sheath. Computers that are generally available can be used to run the program and interface with the equipment. The dentist now records an image of the patient's tooth. FIG. 5 illustrates an example of such a recording. Depending on the type of tooth and the restoration to be produced, the technician or dentist now decides whether a simple or complex layering should be used and what layer thickness is available. The type of field partitions or partial images can also be selected at that time.

Figure 6:
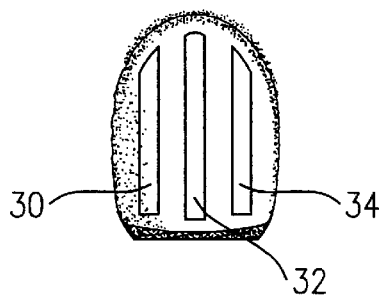
FIG. 6 illustrates another field partition in accordance with FIG. 5.

FIG. 5 also illustrates horizontal partitioning of a patient's tooth 28. The patient's tooth 28 is to be recorded in horizontal partial images as specified by the dentist. Provided for this is a cervical partial image 30 that overlays the tooth, a central partial image 32, and an incisal partial image 34. In addition, in a central area of the screen in a field 36, the dentist indicates the layer thickness that is available to the dental technician. In addition, provided below the field 36 in the illustrated exemplary embodiment, are various switch boxes 38 that make it possible to specify the layering as simple or complex, and that further make it possible to indicate whether horizontal partitioning or vertical partitioning of partial images is desired, or whether freely produced partial images is desired. A view with vertical partial images is illustrated in FIG. 6.

When the partial images are freely selected, the dentist can indicate fields across the tooth using a suitable indicating instrument. A mean is calculated for each partial image and compared to the database. The result can be seen in the results field 40 so that the material selection is specified in detail for the dental technician in terms of shade, layer thickness, layer sequence, and the like.

The type of material, e.g., metal ceramic, non-metal ceramic, or plastic, is either pre-specified from the very beginning or can be specified via additional input fields.

As can be seen from FIG. 5, the partial images 30, 32, and 34 can also be provided as vertical partial images. In this case, the tooth in its entirety is integrated and the layer thickness is optimized according to a pre-specified template such that the incisal region has a larger dental enamel material portion and the cervical region has a larger dentine material portion.

Numerous modifications and further developments of the shade determination apparatus in accordance with the invention are possible without deviating from the field of the invention. For instance, the reference templates 10 can also be produced such that they are arched in order to be able to record the edge effects of the teeth when recording via the covering sheath 20. Another option is to integrate an incisal edge library. In this case, the dentist is provided suggested incisal edges that match the recording of the patient's tooth and that have been produced in a suitable manner and have been stored or even can be obtained from patient data. The tooth or tooth restoration to be produced can also be overlaid with the patient's tooth in order to make a virtual restoration possible and thus to make possible enhanced assessment.

In accordance with a further advantageous embodiment, the shade determination apparatus is also permitted to perform the production of the teeth with CIM technology.

In a further embodiment of the shade determination apparatus in accordance with the invention, a virtual paintbrush may be used in a manner similar to existing image processing programs to construct the tooth virtually. For this, a suitable material, e.g., opaque material, dentine material, or incisal material, is selected, the desired layer thickness is specified, and the region in which the material is to be built up is specified. The shade obtained can be seen immediately on the screen. In this manner, construction can proceed layer by layer, whereby the resultant coloration and transparency effects are immediately visible. Since the natural sample (i.e., the recorded image of the tooth) is in the immediate vicinity, the shade matching can be performed both visually and by comparing color parameters. Using this technique, individual materials can also be exchanged and replaced with suitable materials until the desired effect has been achieved, whereby this technique can be used for crowns, bridges, and direct or indirect fillings.

FIGS. 7–10 illustrate different views of various field partition options, with FIG. 7 illustrating alternatives for horizontal partitioning, while FIG. 8 illustrates variable fields for field partitioning. FIG. 9 illustrates vertical fields for field partitioning, while FIG. 10 illustrates field partitioning with combined vertical and horizontal partitioning. The preferred arrangement is illustrated by FIG. 10, due to the combination of horizontal and vertical partitions.

The opaque layer may be any shade or color. Preferably, the opaque layer is sufficiently light such that it minimizes or avoids affecting the color of the final restoration.

In an additional embodiment of the invention, a digital image of the tooth or dental restoration is provided. Each digital image has a plurality of picture elements, i.e., pixels. Each pixel corresponds to the light intensity and color properties of a given spatial location on the tooth, as recorded by the camera. The distance between adjacent pixels in the image is determined by the spatial resolution of the camera. For example, an image of a tooth shade can be made up of 300 pixels in width across the tooth and 350 pixels in height. Human teeth are similar in size, within a few millimeters, for most people. The central incisors usually measure about 9 to 11 mm in width, and slightly greater in length. Thus, 1 mm of tooth width may be represented by about 30 pixels. By dividing the tooth into pixels, rather than using the entire tooth, or even vertical or horizontal partitions thereof, the color can be more accurately compared and matched.

The invention may further include an electronic analyzing kit. Such a kit may include software to analyze the tooth shade by bands, circles, pixels, or other picture or spatial elements to compare and match the tooth or restoration shade to the reference templates such that almost any color can be matched.

A dental restoration network may be established such that the tooth image information may be shared and transmitted by a dentist who images the tooth and the lab or technician, where such information is received and analyzed. The tooth may be imaged with a digital camera or similar device. The information could be transmitted to the lab by any available media, but preferably via a communications network, such as a diskette or CD that is shared by the dentist and the technician, via e-mail, or more preferably, via the Internet or direct electronic connection, such as would be transmitted by a modem. Once the information is transmitted to and received by the lab, the information may be downloaded onto one or more computers that may be accessed by technicians. The shade information may then be analyzed by the software package to determine the shade of the tooth on a pixel-by-pixel basis. The technician may then use this information to map certain regions of the tooth where the shade is similar. Once a restoration has been suggested or produced, the technician my transmit the information back to the dentist via a communications network that is the same or different from the one detailed above. With appropriate coordination, these analyses can be made in real time, with the patient in the dentist's chair and the laboratory technician viewing the transmitted image on his monitor or other display.

The computer program contains a database of restoration layer or porcelain colors. The computer may then suggest or provide layering sequences to the technician to help determine how to build up layers of different colors on the tooth, such that the suggested layer combination matches the desired tooth color. The computer may also be used to convert its pixel analysis to a mapping system. This would facilitate building up the layers of restorative material, since this is usually done by regions of the tooth, rather than on a pixel-by-pixel basis.

In another embodiment, the dentist may take a photograph or other image of the tooth to accompany the pixel image. In this way, the restoration technician can used added judgment, if necessary, when using the software package. For example, tooth areas that are relatively dark could use different porcelain combinations from tooth areas that are relatively light in color.

Referring again to FIGS. 7–10, for example, the cervical partial image 30, the central partial image 32, and the incisal partial image 34 may be mapped regions of the tooth, wherein the shade is similar. The computer may suggest a particular layering scheme to build up each of these regions separately, based on the different starting shade of each region.

The computer database may further contain information on tooth shapes. In this case, it may be necessary for the scanned image to contain images of a plurality of teeth, or even the entire mouth of the patient. In this way, the database may analyze the patient's teeth shape for enhanced smile appearance, and improved bite between the upper and lower teeth, and improved chewing to minimize or avoid further wear on the restoration and surrounding teeth. The database would contain preferred tooth shapes as well as an incisal edge library, such that the software could suggest to the technician a preferred tooth shape or incisal edge for a particular restoration. As the layers are built up, they can be shaped to improve the patient's appearance. The restoration could then be prepared for not only optimum color, but also for optimum shape of the tooth.

The term "about," as used herein, should generally be understood to refer to both numbers in a range of numerals. Moreover, all numerical ranges herein should be understood to include each whole integer within the range.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method for determining a patient's tooth shade for replacement or restoration thereof, which comprises:

generating at least a partial electronic image of a patient's tooth wherein the image includes color information representative of the patient's tooth shade;

electronically storing color information representative of a plurality of tooth shades in the form of a set of reference templates produced in a layer arrangement and including at least one of layer thickness or material selection; and comparing the color information of the image with the stored tooth shade color information to identify reference templates that may be used to prepare a tooth replacement or restoration having a color that corresponds to the patient's tooth shade.

2. The method of claim 1 wherein the image of the patient's tooth is electronically compared to the stored color information, each reference template includes one or more layers of dentine material, incisal material, or opaque material, and wherein the comparing of color information and the identification of the reference template(s) is performed by a computer.

3. The method of claim 2, wherein the computer controls a CIM apparatus by which the layering of the replacement tooth or restoration to be manufactured can be determined in terms of material selection and layer thickness so that the replacement tooth or restoration can at least be prefabricated.

4. The method of claim 1 wherein the reference templates are made of materials that are fired at the same temperature and same firing curve as the materials that are to be used for the replacement tooth or restoration to provide the closest color match.

5. The method of claim 1 wherein a full image of the patient's tooth is mapped with color pixels to assist in determining the color of the patient's tooth shade, and further a matching reference template is determined by selecting one or more pixels of the image, which pixels correspond to differential spatial locations of the patient's tooth, that provide similar color information and electronically comparing that color information with the stored reference template color information to determine the color of that portion of the patient's tooth.

6. The method of claim 5 wherein the patient's tooth is mapped with pixel colors that are projected onto a display and the reference templates are viewable on the display adjacent the patient's tooth so that optimum visual color matches can be made.

7. The method of claim 5, wherein the patient's tooth color is determined by averaging the color information at selected pixel locations of the image before electronically comparing the averaged color information with the stored reference template color information.

8. The method of claim 5 wherein selection of the pixel(s) and determination of reference template(s) are repeated until a tooth shade color is determined for vertical or horizontal partitions, or both, of the tooth and until all the tooth shade color is determined for all spatial locations of the image of the patient's tooth.

9. The method of claim 5, wherein, prior to producing the replacement tooth or tooth restoration, the selected reference template(s) can be overlaid on the tooth shape on a display so that a virtual tooth replacement or restoration can be viewed along with an adjacent tooth or teeth.

10. The method of claim 1 which further comprises utilizing a digital camera to obtain the image of the patient's tooth and utilizing the same camera or similar metamerical conditions to obtain the color information of the reference templates before electronically storing the color information of the reference templates.

11. The method of claim 1 which further comprises electronically storing the patient's tooth shade color(s) and selected reference template(s) on an electronic storage medium and then subsequently forwarding the medium to a dental laboratory for use in construction of a replacement tooth or reconstruction of the patient's tooth.

12. The method of claim 11 wherein the electronic storage medium is transmitted to the dental laboratory over a communications network.

13. The method of claim 12, wherein the electronic medium includes computer memory, a diskette, or a compact disk and the communications network comprises a computer, e-mail or the internet.

14. The method of claim 1, which further comprises electronically storing preferred tooth shapes, incisal edges or tooth preparations to assist the dentist in enhancing the preparation of the patient's tooth or the shape or incisal edge of the restoration or replacement tooth to provide improved smile appearance or improved biting or chewing performance.

15. The method of claim 14, wherein each layer has a thickness of between about 0.3 and 3 mm and the materials are made of glass-ceramics or fiber-reinforced plastic.

16. The method of claim 1, which further comprises applying one or a plurality of layers of dentine material, enamel material or opaque material to a desired thickness to produce a restoration having the desired color.

17. The method of claim 1, wherein the reference templates are stored in a database on a computer.

18. A method for determining a patient's tooth shade for replacement or restoration thereof, which comprises:

generating at least a partial electronic image of a patient's tooth wherein the image includes color information representative of the patient's tooth shade;

electronically storing color information representative of a plurality of tooth shades in the form of a set of reference templates produced in a layer arrangement and including layer thickness and material selection; and comparing the color information of the image with the stored tooth shade color information to identify reference templates that may be used to prepare a tooth replacement or restoration having a color that corresponds to the patient's tooth shade.

* * * * *